United States Patent [19]

Jones

[11] Patent Number: 5,176,918
[45] Date of Patent: Jan. 5, 1993

[54] TOPICAL MEDICAMENT

[76] Inventor: Jeffry L. Jones, P.O. Box 2394, Big Spring, Tex. 79721

[21] Appl. No.: 633,018

[22] Filed: Dec. 20, 1990

[51] Int. Cl.$^5$ ............................................... A61K 9/06
[52] U.S. Cl. .................................. 424/449; 424/686; 424/717; 514/825
[58] Field of Search ............... 424/717, 449, 401, 686; 514/825, 947

[56] References Cited

U.S. PATENT DOCUMENTS 4,933,184  6/1990  Tsuk ..................................... 424/449

OTHER PUBLICATIONS

Remington's Pharmaceutical Sciences Treatise, Mack Publishing Co., 1990, pp. 819–820.

Primary Examiner—Thurman K. Page
Assistant Examiner—D. Colucci
Attorney, Agent, or Firm—Edward L. Bowman

[57] ABSTRACT

A topical medicament comprising a dilute aqueous solution of sodium bicarbonate and a transdermal carrier, preferably containing approximately equal proportions by weight of a 3 percent aqueous solution of sodium bicarbonate, and propylene glycol, the resultant solution comrpising about 1.5 weight percent sodium bicarbonate.

13 Claims, No Drawings 5,176,918

TOPICAL MEDICAMENT

TECHNICAL FIELD

This invention relates to a topical medicament, and more particularly, to a composition comprising sodium bicarbonate, distilled water, and an absorptive transdermal carrier such as propylene glycol.

BACKGROUND OF THE INVENTION

Topical medicaments previously used for treating or relieving symptoms such as body odor, itching, sunburn, minor burns, minor inflammatory diseases, sore and strained muscles, and the like, have long been treated through the use of topical anesthetics and analgesics.

Dentifrice gels containing sodium bicarbonate in an aqueous carrier comprising propylene glycol have previously been disclosed in U.S. Pat. No. 4,943,429.

An effective, medicament is needed, however, that is easily absorbable through the skin, is non-toxic, odorless, stainless, non-greasy, contains no aluminum salts, and is relatively inexpensive. Such a composition is provided herein.

SUMMARY OF THE INVENTION

According to one embodiment of the invention, a topical medicament is provided that comprises from about 0.25 percent to about 3 percent by weight sodium bicarbonate, from about 1 to about 99 percent by weight of a transdermal carrier, and water.

According to another embodiment of the invention, a topical medicament is provided that comprises from about 0.25 to about 3 weight percent sodium bicarbonate, from about 1 to about 99% weight percent propylene glycol, and water.

According to a particularly preferred embodiment of the invention, a topical medicament is provided that comprises about 1.5 weight percent sodium bicarbonate in about 50 weight percent distilled water, and about 50 weight percent propylene glycol.

An alternate preferred embodiment of the invention has from about 0.1 to about 0.5 weight percent menthol added to the solution. Menthol is a differential anesthetic with a pleasing odor and gives a sensation of coolness to increase the therapeutic effect.

DETAILED DESCRIPTION OF THE INVENTION

Applicant has surprisingly discovered that a very effective topical medicament can be made by mixing a dilute aqueous solution of sodium bicarbonate with an absorbent transdermal carrier such as propylene glycol. The subject composition is useful for relieving itching and pain from sunburn, minor burns, sore and strained muscles, insect bites, minor inflammatory diseases such as arthritis, tendinitis or bursitis, and the like. Because both sodium bicarbonate and propylene glycol are approved for topical use by the FDA, the composition of the invention is believed to be non-toxic.

It will be appreciated by those of ordinary skill in the art upon reading this disclosure that the compositions of the invention can be made with widely ranging proportions of the sodium bicarbonate and transdermal carrier components. Compositions comprising approximately equal proportions of a dilute aqueous solution of sodium bicarbonate and a transdermal carrier are generally preferred. It is only required, however, that sufficient transdermal carrier be present to cause adequate absorption of the subject medicament into the skin of the user to alleviate the particular symptom being treated. Maximum therapeutic results were achieved in solutions containing less than 3 weight percent sodium bicarbonate solutions containing about 1.5 weight percent sodium bicarbonate are preferred due to safety of 1.5% being isotonic with human tissue (American Hospital Formulary Service Drug Information 1987).

Another preferred composition of the invention comprises about 2.5 weight percent sodium bicarbonate dissolved in water, and about 25 weight percent propylene glycol.

Preferred compositions for use in preparing the topical medicaments of the invention are made by dissolving from about 0.5 to about 6, and most preferably about 3, weight percent sodium bicarbonate in distilled water and thereafter combining the dilute aqueous solution of sodium bicarbonate thus formed with a transdermal carrier such as propylene glycol in approximately equal proportions by weight. This results in a medicament comprising from about 0.25 to about 3 weight percent, and most preferably about 1.5 weight percent sodium bicarbonate in solution.

The transdermal carrier component of the inventive composition is preferably selected from the group of non-toxic water-soluble or miscible materials that are capable of being absorbed through human skin together with at least a minor amount of the sodium bicarbonate. Although propylene glycol is the preferred transdermal carrier for use in the compositions of the invention, examples of other transdermal carriers that are believed to be satisfactory for use in the subject compositions include: polyethylene glycol 400, glycerin and sorbitol.

While the sodium bicarbonate and the transdermal carrier components are most significant to the compositions of the invention, it will be understood and appreciated by those of ordinary skill in the art upon reading this disclosure that other coloring agents, fragrances, moisturizers, lotions, creams and the like can also be compounded with the composition of the invention to produce a commercially marketable topical medicament.

Thus, for example, from about 0.1 to about 0.5 weight percent menthol can be added to the solution to provide a pleasing odor and give a sensation of coolness upon topical application by the user. Where menthol is added as an ingredient in the topical medicaments of the invention, it is preferably dissolved in the propylene glycol or other transdermal carrier prior to combining that component with the aqueous solution of sodium bicarbonate. Similarly, soluble rose can be added to the formulation for fragrance.

It will also be apparent to one of ordinary skill in the art upon reading this disclosure that a hydrophilic ointment can be combined with the formulation disclosed herein to provide a topical medicament that is an ointment rather than a solution.

The compositions disclosed herein can be made by solubilizing sodium bicarbonate directly into propylene glycol, but solutions comprising from about 0.25 to about 75 weight percent propylene glycol together with an aqueous solution comprising from about 0.025 to about 3 weight percent sodium bicarbonate (by weight of the total solution) are preferred. The compositions of the invention, and the beneficial effects achieved through the use thereof, are further described in relation to the following examples:

EXAMPLE 1

A topical medicament was made by mixing approximately equal weights of propylene glycol and an aqueous solution containing about 1.5 weight percent sodium bicarbonate by weight of the total mixture. The subject medicament was topically applied by several users and was found to be effective for relieving pain and discomfort due to arthritis, leg cramps, itching due to insect bites, itching due to dry skin, lower back pain, and minor burns.

EXAMPLE 2

A topical medicament was prepared as for example 1, but with the further addition of 0.5 percent menthol and the resulting medicament was applied topically and exhibited the beneficial effects noted above, together with an immediate cooling sensation that is attributable to the menthol component.

EXAMPLE 3

A topical medicament was prepared by combining 50 weight percent propylene glycol with 50 weight percent of an aqueous solution comprising 3 percent sodium bicarbonate by weight of the total solution. The topical medicament was found to be as effective as the composition of Example 1 for relieving pain and itching.

EXAMPLE 4

A topical medicament was prepared by mixing 50 weight percent propylene glycol with 50 weight percent of an aqueous solution further comprising 0.1 weight percent sodium bicarbonate by weight of the total medicament. The resultant product was applied topically, but no observable relief of pain or itching occurred.

EXAMPLE 5

A topical medicament was prepared comprising about 50 weight percent propylene glycol and about 50 percent of an aqueous solution further comprising 0.25 weight percent sodium bicarbonate by total weight of the medicament. Following topical application of the medicament for the relief of pain and itching, some relief was observed, but less than that experienced with the topical medicament containing 1.5 weight percent sodium bicarbonate by weight of the total composition.

EXAMPLE 6

A topical medicament was prepared by mixing 1 weight percent sodium bicarbonate into 99 weight percent propylene glycol. The resultant medicament was fully effective for the temporary relief of pain and itching.

EXAMPLE 7

A topical medicament was prepared comprising 50 weight percent sorbitol and 50 weight percent of an aqueous solution further comprising 1.5 weight percent sodium bicarbonate by weight of the total compositions. The following topical application for the relief of pain and itching, the medicament was found to be effective, but slower acting than the compositions comprising propylene glycol.

EXAMPLE 8

A topical medicament was prepare comprising 50 weight percent glycerin and 50 weight percent of an aqueous solution further comprising 1.5 weight percent sodium bicarbonate by weight of the total composition. The results achieved following topical application of the medicament were the same as those for the composition prepared in Example 7.

From the foregoing examples, it is seen that the topical medicament comprising sodium bicarbonate in an amount ranging from at least about 0.25 weight percent up to about 3 weight percent is effective in reducing muscle and joint pain, and itching of the skin. Compositions comprising a lesser amount of sodium bicarbonate appear to lose this effectiveness.

Similarly, while other transdermal carrier such as sorbitol and glycerine appear to be somewhat effective when used in topical medicaments comprising sodium bicarbonate in the percentage ranges disclosed herein, the use of propylene glycol in the subject compositions appears to provide the most rapid results in terms of delivering sodium bicarbonate transdermally to the point of origin of the pain or itching.

Although percentages of propylene glycol in excess of 50 weight percent can be used in the compositions of the invention, they do not appear to be necessary to achieve the desired results. Also, while the amount of sodium bicarbonate can be increased above 3 weight percent of the total composition, undesirable precipitation of the sodium bicarbonate out of solution can occur where greater amounts are used.

Other alterations and modifications of the invention disclosed and claimed herein will likewise become apparent upon reading the present disclosure, and it is intended to cover all such alterations and modifications as may fall within the broadest interpretation of the appended claims to which the inventor is legally entitled.

I claim:

1. A topical analgesic composition consisting essentially of water, about 0.25 to about 3 weight percent sodium bicarbonate, and about 1 to about 99 weight percent of a non-toxic water-soluble or water-miscible transdermal carrier selected from the group consisting of propylene glycol, polyethylene glycol, sorbitol, and glycerin, said weight percentages being based on the weight of the composition as a whole and said three essential ingredients making up at least about 99.5 weight percent of said composition.

2. A composition according to claim 1 containing about 1 to about 50 eight percent of said transdermal carrier.

3. A composition according to claim 2 containing about about 1 to about 3 weight percent sodium bicarbonate.

4. A composition according to claim 1 wherein said transdermal carrier is propylene glycol.

5. A composition according to claim 4 containing about 1 to about 50 weight percent propylene glycol.

6. A composition according to claim 5 containing about about 1 to about 3 weight percent sodium bicarbonate.

7. A composition according to claim 6 containing about 50 weight percent propylene glycol.

8. A composition according to claim 7 containing about 1.5 weight percent sodium bicarbonate.

9. A composition according to claim 4 containing about 1 to about 25 weight percent propylene glycol.

10. A method for treating the pain associated with sore muscles, arthritis, tendinitis, and bursitis comprising applying to the affected area an effective amount of a topical analgesic composition consisting essentially of water, about 0.25 to about 3 weight percent sodium bicarbonate, and about 1 to about 99 weight percent of a non-toxic water-soluble or water-miscible transdermal carrier selected from the group consisting of propylene glycol, polyethylene glycol, sorbitol, and glycerin, said weight percentages being based on the weight of the composition as a whole and said three essential ingredients making up at least about 99.5 weight percent of said composition.

11. A method according to claim 10 wherein said transdermal carrier is propylene glycol.

12. A method according to claim 11 wherein said composition contains about 50 percent propylene glycol.

13. A method according to claim 12 wherein said composition contains about 1.5 weight percent sodium bicarbonate.

* * * * *